United States Patent [19]

Gammon

[11] 4,274,716
[45] Jun. 23, 1981

[54] OCULAR FIXATION DEVICE

[76] Inventor: James A. Gammon, 8907 Winands Rd., Randallstown, Md. 21133

[21] Appl. No.: 55,042

[22] Filed: Jul. 5, 1979

[51] Int. Cl.³ .......................... A61B 3/10; A61B 3/02; A61B 3/00
[52] U.S. Cl. ...................................... 351/36; 351/16; 351/38
[58] Field of Search .................. 351/36, 6, 16, 24, 32, 351/37, 38, 1

[56] References Cited

U.S. PATENT DOCUMENTS

| 3,421,498 | 1/1969 | Gans ........................................ 351/24 |
| 4,063,807 | 12/1977 | Gelius et al. ............................ 351/24 |

Primary Examiner—John K. Corbin
Assistant Examiner—Rodney B. Bovernick
Attorney, Agent, or Firm—Manfred M. Warren; Robert B. Chickering; Glen R. Grunewald

[57] ABSTRACT

An ocular fixation device for mounting on an ophthalmological examination instrument used for examining the eyes of a patient comprises a pair of light emitters mounted for individual left and right eye viewing by the patient. The light emitters are connected to an electric circuit which enables an examiner to selectively, individually energize the light emitters, thus fixing the patient's gaze as required for certain examination and treatment procedures.

6 Claims, 5 Drawing Figures

OCULAR FIXATION DEVICE

BACKGROUND OF THE INVENTION

1. Field of the Invention

The invention relates generally to ophthalmological examination instruments and more particularly to fixation targets for attracting and holding the gaze of a patient.

2. Description of Prior Art

In order to perform certain opthalmological procedures such as tonomet, foreign body removal, and fundus photography, it is desirable to fix the eyes of the patient in the approximately straight ahead gaze position. Various ocular fixation devices have been disclosed which are used to attract and hold the visual attention of the patient so as to orient and fix the eyes in the desired gaze portion. Such devices usually include a target such as a light, or animated object upon which the patient is instructed to direct his vision. An example of a typical ocular fixation device is disclosed in U.S. Pat. No. 4,093,359 (Ketcham). The Ketcham invention comprises an animated fixation target such as a toy animal having movable body parts whose movement can be controlled by the examiner, so as to hold the visual attention of the patient.

The most common type of prior art ocular fixation devices centers around the use of a single movable light target, such as the one disclosed in U.S. Pat. No. 3,897,141 (Schocket). The Schocket device comprises a small tight adapted to be moved in a circular path around and above the patient's face. The Schocket device is typical of fixation devices which are currently in wide use among ophthalmologists. A further example of a related fixation device is found in U.S. Pat. No. 3,871,753 (Papritz), which also employs a single light target which is movable.

U.S. Pat. No. 3,484,155 (Praeger) discloses the use of a movable primary illuminated target and an ancillary stationary illuminated target, both of which are mounted on the head of the examiner. One disadvantage common to all of the prior art devices is that their operation requires repositioning of an illuminated target. The transmission of electrical energy to the movable target requires the use of wipers, brushes, slip rings, and the like. It is well known that these movable electrical contacts significantly reduce the reliability of the devices and greatly increase their cost. Even the Praeger device which discloses the use of two illuminated targets employs a wiper assembly for transmitting electrical power to the movable primary target.

All of the prior art devices require a repositioning of a fixation target during the normal course of their operation. Another major disadvantage in the aforementioned devices is that the supporting structure for the movable fixation target can interfere with or even collide with the patient or the examination equipment. The cords, wiper arm and slip ring assemblies, and other complex structural components of the prior art devices detract from their reliability and usefulness.

SUMMARY OF THE INVENTION

An object of the present invention is to provide an ocular fixation device with optimal fixation qualities without requiring the use of a movable illuminated fixation target.

Another object of the present invention is to provide a device which eliminates patient-examiner right-left ambiguity and confusion by employing distinctively different colored illuminated fixation targets for the patient's right and left eye.

A further object of the present invention is to provide a simple, easily and readily applied fixation device formed for mounting on a conventional slit lamp examination device having a binocular microscope and provisions for a cough shield.

A still further object of the present invention is to incorporate the device of the present invention on and within the confines of a structure which serves as a cough shield.

Still another object is to provide an ocular fixation device having a self-contained power source having a long useful life.

Still a further object of the present invention is to provide permanently positioned light emitting targets, one opposite each eye thereby eliminating all rotating, movable, or flexible supports and the complex electrical transmission structures attendant to their use.

The invention possesses other objects and features of advantage, some of which of the foregoing will be set forth in the following description of the preferred form of the invention which is illustrated in the drawings accompanying and forming part of this specification. It is to be understood, however, that variations in the showing made by the said drawings and description may be adopted within the scope of the invention as set forth in the claims.

DETAILED DESCRIPTION OF THE INVENTION

Figure 1:
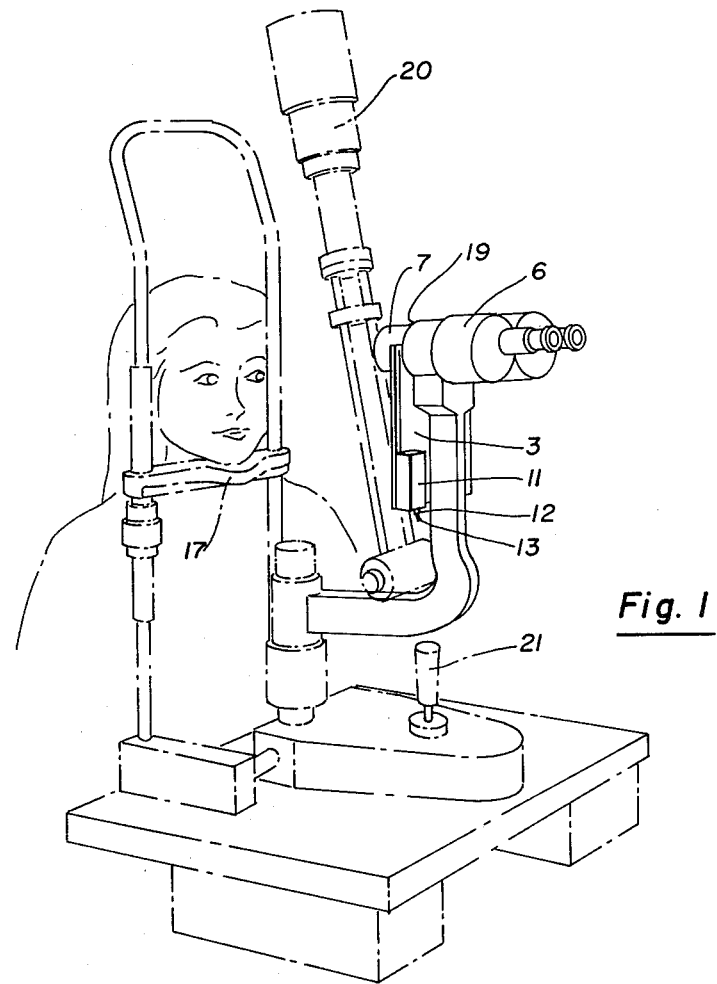
FIG. 1 is a perspective view of the preferred embodiment of the device mounted on the binocular microscope housing of a conventional slit lamp examination instrument.

The ocular fixation instrument of the present invention is formed for mounting on an ophthalmological examination instrument used for examining the eyes of a patient and comprises a pair of light emitters 1 and 2 mounted on a transparent shield 3 for individual left and right eye viewing by the patient. An electric circuit is connected to light emitters 1 and 2 through conductor pairs 5 and 6 and is configured so as to enable an examiner to selectively, individually energize either light emitter 1 or light emitter 2 for the purpose of attracting and holding the gaze of a patient.

In FIG. 1, the preferred embodiment of the invention is seen to comprise a structure which conveniently replaces the conventional transparent cough shield, usually associated with the use of binocular opthalmological examination microscopes. As can be seen in FIG. 1, the preferred form of the invention adds very little structural volume to that normally occupied by the cough shield thus minimizing interference with the normal operation of the examination instrument. In FIG. 1 binocular microscope 6 is seen to have a cylindrical lens housing 7. Shield 3, in the preferred embodiment, has a circular cutout 8 at its normally upper end which is formed to fit around the periphery of housing 7. The shield 3 has a hole 18 which facilitates fastened mounting against the shoulder 19 of lens housing 7. The structure of the shield 3 extends laterally from the periphery of circular cutout 8 so as to provide vertically upstanding shield portions 9 and 10. Light emitters 1 and 2 are mounted on shield portions 9 and 10, respectively. In the preferred embodiment, light emitters 1 and 2 are distinctively different colored light emitting diodes.

Figure 2:
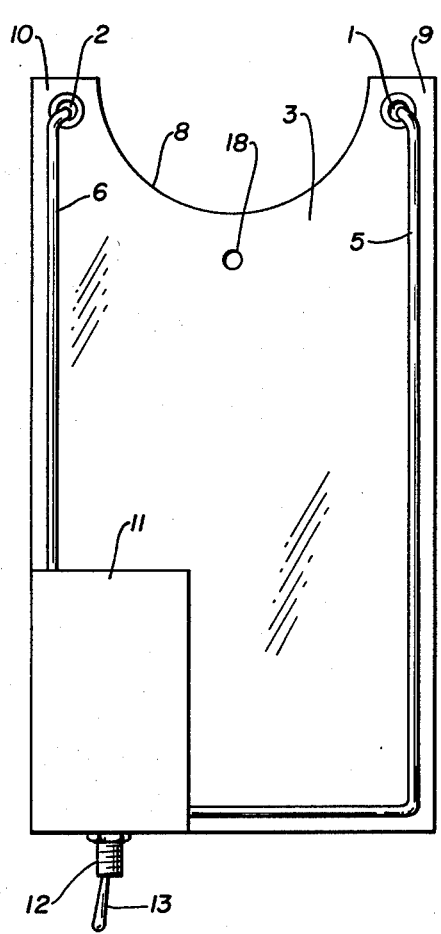
FIG. 2 is a rear view of the fixation device illustrated in FIG. 1.
Figure 3:
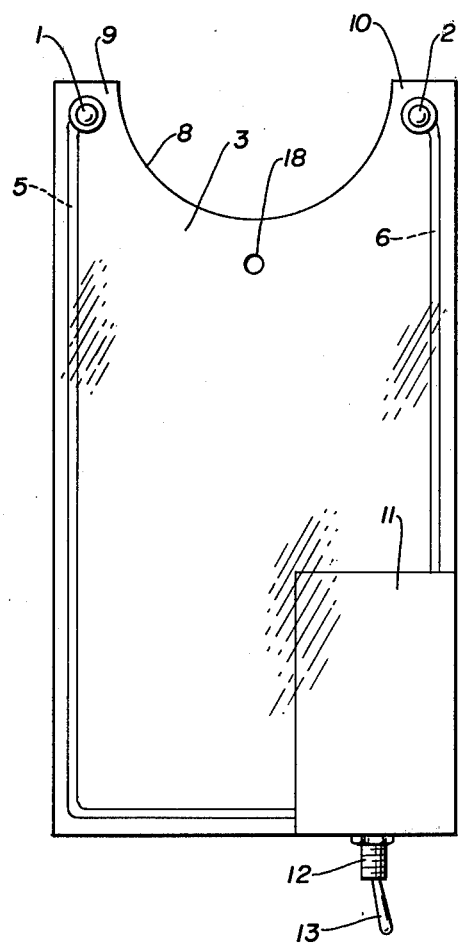
FIG. 3 is a front view of the device illustrated in FIG. 1.
Figure 4:
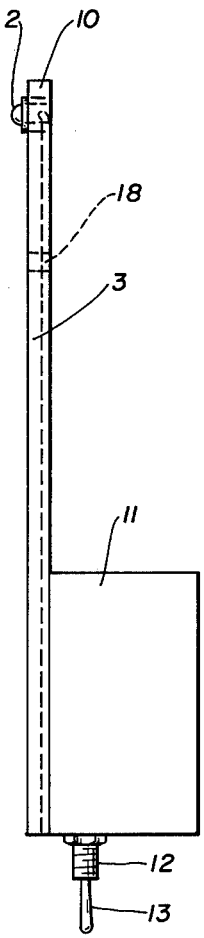
FIG. 4 is a side view of the device illustrated in FIG. 1.

As seen in FIGS. 2 and 3, light emitters 1 and 2 are mounted on transparent shield 3 in a normally horizontally spaced relation which corresponds generally to the interpupillary spacing of the patient. The electrical circuitry of the device is enclosed in housing 11 which is mounted on a normally lower portion of shield 3. The electric circuit includes a switch 12 having a switch arm 13 which depends from housing 11 and extends below the normally lower end of shield 3 for engagement and displacement by the examiner.

Figure 5:
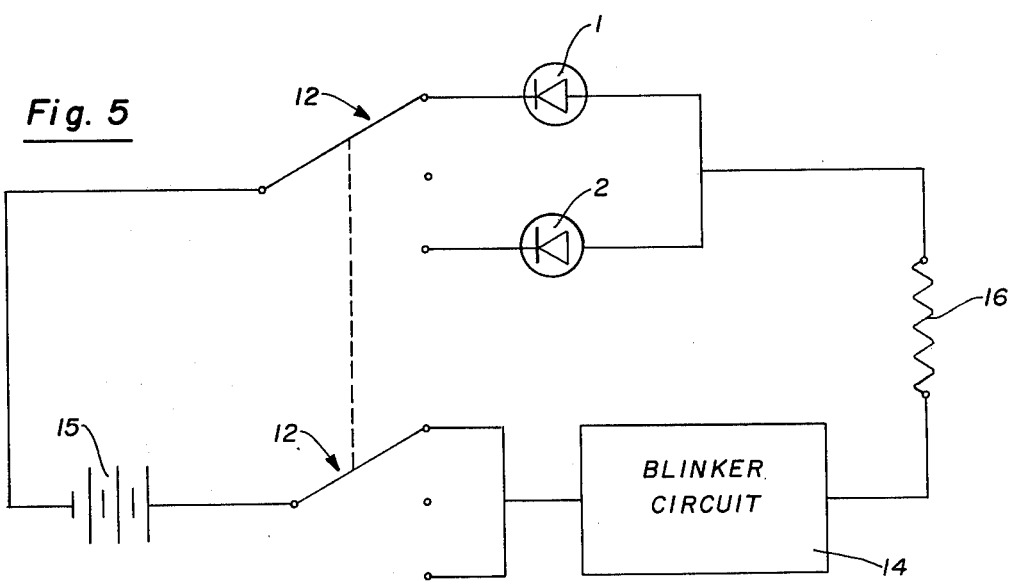
FIG. 5 is an electrical schematic diagram of the preferred embodiment of the device.

Referring to FIG. 5, the electrical circuit used in the preferred embodiment of the device comprises a battery 15, a three position center off double pole, double throw toggle switch 12, a blinker circuit 14, a current limiting resistor 16 and light emitters 1 and 2, shown here as light emitting diodes.

As can be seen by examining the schematic diagram of FIG. 5, wherein switch 12 is in its center position, power is interrupted and the light emitters are not energized. When switch 12 is thrown into either the left or right position, power is supplied to either light emitter 1 or light emitter 2 through blinker circuit 14 and current limiting resistor 16. Blinker circuit 14 periodically interrupts the current flow so as to cause blinking of the selected light emitter. In the preferred embodiment, a CMOS chip is used to perform the blinking function, however, any commonly known electronic or electromechanical blinker may be employed. Current limiting resistor 16 is used to limit a current which flows through the light emitters to a level which does not exceed their specifications.

As seen in FIG. 1, the housing 11 which encloses the previously described circuitry is mounted on the side of the shield which is normally opposite from the patient being examined. Often, in the use of prior art fixation devices, the patient is uncertain whether to concentrate on the light of the fixation target or the usually brighter light of the examination instrument, e.g. slit lamp light. Further confusion is caused by the fact that the examiner sits opposite the patient, hence the patient's right side becomes the examiner's left side and instructions to the patient can be confusing for both parties. This ambiguity and confusion is positively eliminated by the use, in the present invention, of distinctively different colored light emitters which are positioned so as to place one in front of the patient's left eye and one in front of the right eye. No reference need be made to right or left and the patient can merely be instructed to look at the green light or the red light, depending upon which is selectively energized by the examiner. The use of light emitting diodes with their attendant reliability, long life, and low current drain, allows the use of a small self-contained battery pack within housing 11 which, in normal use, can last many months. The simple fixation device of the instant invention has no moving parts other than the toggle switch 12. The device is easily incorporated into the structure of a cough shield of the type usually affixed to a binocular eye examination microscope. Actual operation of the fixation device of the present invention is best understood by referring to FIG. 1. The patient's head is positioned so that the chin is supported by chin rest 17. Lamp 20 is a slit-type lamp which illuminates the patient's eye for microscopic examination. The mirrors which transmit the light from lamp 20 to the patient's eye have been eliminated from the drawing so as not to obscure the illustration of the fixation device. Fixation of either the patient's right or left eye is accomplished by moving switch arm 13 so as to illuminate the appropriate light emitter. Switch arm 13 is positioned so that it extends below the normally lower end of shield 3, thus allowing unimpeded access by the examiner. Single handed operation of both the slit lamp and the fixation device is made possible by the switch arm 13 position above and proximate to the slit lamp focusing lever 21. The focusing lever 21 is customarily grasped and operated by the examiner's hand. The thumb of this same hand can then extend upward and deflect the fixation device switch arm 13 as required. The device of the present invention has been found to provide optimal fixation qualities in connection with a variety of ophthalmological procedures including retinal evaluation, ophthalmic photography, foreign body removal, tonometry, and the like.

What is claimed is:

1. An ocular fixation device for use with a binocular microscope ophthalmological instrument used for examining the eyes of a patient comprising:
    a pair of light emitters;
    electric circuit means connected to said emitters enabling an examiner to selectively, individually energize said emitters;
    a transparent shield formed for mounting on said microscope substantially perpendicular to the optical axes thereof; and
    said emitters being mounted on said shield in a normally horizontal spaced relation corresponding generally to the interpupillary spacing of the patient for individual left and right eye viewing by the patient.

2. The device of claim 1, said emitters emanating when energized distinctively different colored lights.

3. The device of claim 1,
    said light emitters comprising light emitting diodes.

4. The device of claim 1,
    said microscope having a cylindrical lens housing;
    said shield having a circular cutout at its normally upper end formed to fit around the periphery of said lens housing and defining horizontally spaced vertically upstanding shield portions; said emitters being mounted on said portions.

5. The device of claim 4,
    a housing mounted on a normally lower portion of said shield, said electric circuit means being mounted in said housing and including an electric switch having a switch arm depending from said housing and below the normally lower end of said shield for engagement and displacement by the examiner.

6. The device of claim 5, one side of said shield normally facing the patient and the opposite side of said shield normally facing the examiner;
    said housing being mounted on said opposite side of said shield.

* * * * *